(12) United States Patent
Pack et al.

(10) Patent No.: US 6,692,935 B1
(45) Date of Patent: Feb. 17, 2004

(54) TARGETED HETERO-ASSOCIATION OF RECOMBINANT PROTEINS TO MULTI-FUNCTIONAL COMPLEXES

(75) Inventors: Peter Pack, Oberfohring (DE); Andrei Lupas, Unterhaching (DE)

(73) Assignee: MorphoSys AG, Martinsried (DE)

( * ) Notice: Subject to any disclaimer, the term of this patent is extended or adjusted under 35 U.S.C. 154(b) by 21 days.

(21) Appl. No.: 09/583,808

(22) Filed: May 30, 2000

Related U.S. Application Data

(63) Continuation of application No. 08/817,787, filed as application No. PCT/EP95/04117 on Oct. 20, 1995, now Pat. No. 6,294,353.

(30) Foreign Application Priority Data

Oct. 20, 1994 (EP) .............................................. 94116558

(51) Int. Cl.[7] .......................... C12P 21/06; C07K 14/00; C07H 17/00
(52) U.S. Cl. ................ 435/69.1; 435/320.1; 435/252.3; 435/325; 536/23.1; 530/350
(58) Field of Search ........................ 530/350; 435/69.1, 435/320.1, 252.3, 325; 536/23.1

(56) References Cited

FOREIGN PATENT DOCUMENTS

| EP | A 0 404 097 A3 | 12/1990 |
|---|---|---|
| WO | WO A 92/10209 | 6/1992 |
| WO | WO A 93/11162 | 6/1993 |
| WO | WO A 93/15210 | 8/1993 |
| WO | WO A 94/20140 | 9/1994 |

OTHER PUBLICATIONS

Katagiri et al. 1992; Mol. Cell. Biol. 12(11): 4809–4816.*
Loetscher et al. 1991; J. Biol. Chem. 266(27): 18324–18329.*
Schnee et al. 1987; PNAS 84 :6904–6908.*
De Prat Gay, G. et al., The structure of the transition state for the association of two fragments of the barley chymotrypsin inhibitor 2 to generate native–like protein: Implications for mechanisms of protein folding, *Proc. Natl. Acad. Sci USA*, 91, 10943–10946 (1994).
De Prat Gay, G. et al., Generation of a family of protein fragments for structure–folding studies. Kinetics of association of the two chymotrypsin inhibitor–2 fragments, *Biochemistry*, 33, 7964–7970 (1994).
Johnsson, N. and Varshavsky, A., "Split Ubiquitin as a Sensor of Protein Interactions in vivo", *National Academy of Science Proceedings*, 91, 10340–10344 (1994).
Kippen, A.D. et al., Folding of Barnase in parts, *Biochemistry*, 33, 3778–3786 (1994).
Kippen, A.D. and Fersht, A.R., Analysis of the mechanism of assembly of cleaved Barnase from two peptide fragments and its relevance to the folding pathway of uncleaved Barnase, *Biochemistry*, 34, 1464–1468 (1995).
Pack, P., Dissertation zur Erlangung des Doktorgrades der Fakultat fur Chemie und Pharmazie der Ludwig–Maximilians–Universitat Munchen: Mini–Antikorper. Bivalenta, tetravalente und bispezifische Immunoglobuline aus *E. Coli.*, (1994).
Ruiz–Sanz, J. et al., Protein fragments as models for events in protein folding pathways: protein engineering analysis of the association of two complementary fragments of the Barley Chymotrypsin Inhibitor 2 (CI–2), *Biochemistry*, 34, 1695–1701 (1995).

* cited by examiner

*Primary Examiner*—Karen Cochrane Carlson
(74) *Attorney, Agent, or Firm*—Heller Ehrman White & McAuliffe LLP

(57) ABSTRACT

The present invention relates to a method for targeted assembly of distinct active peptide or protein domains into a single complex and to such complexes. The invention relates particularly to the fusion of peptide or protein domains to complementary association domains which are derived from a single tertiary or quaternary structure by segmentation. The association domains are designed to assemble in a complementary fashion, thereby providing multifunctional (poly)peptides.

26 Claims, 15 Drawing Sheets

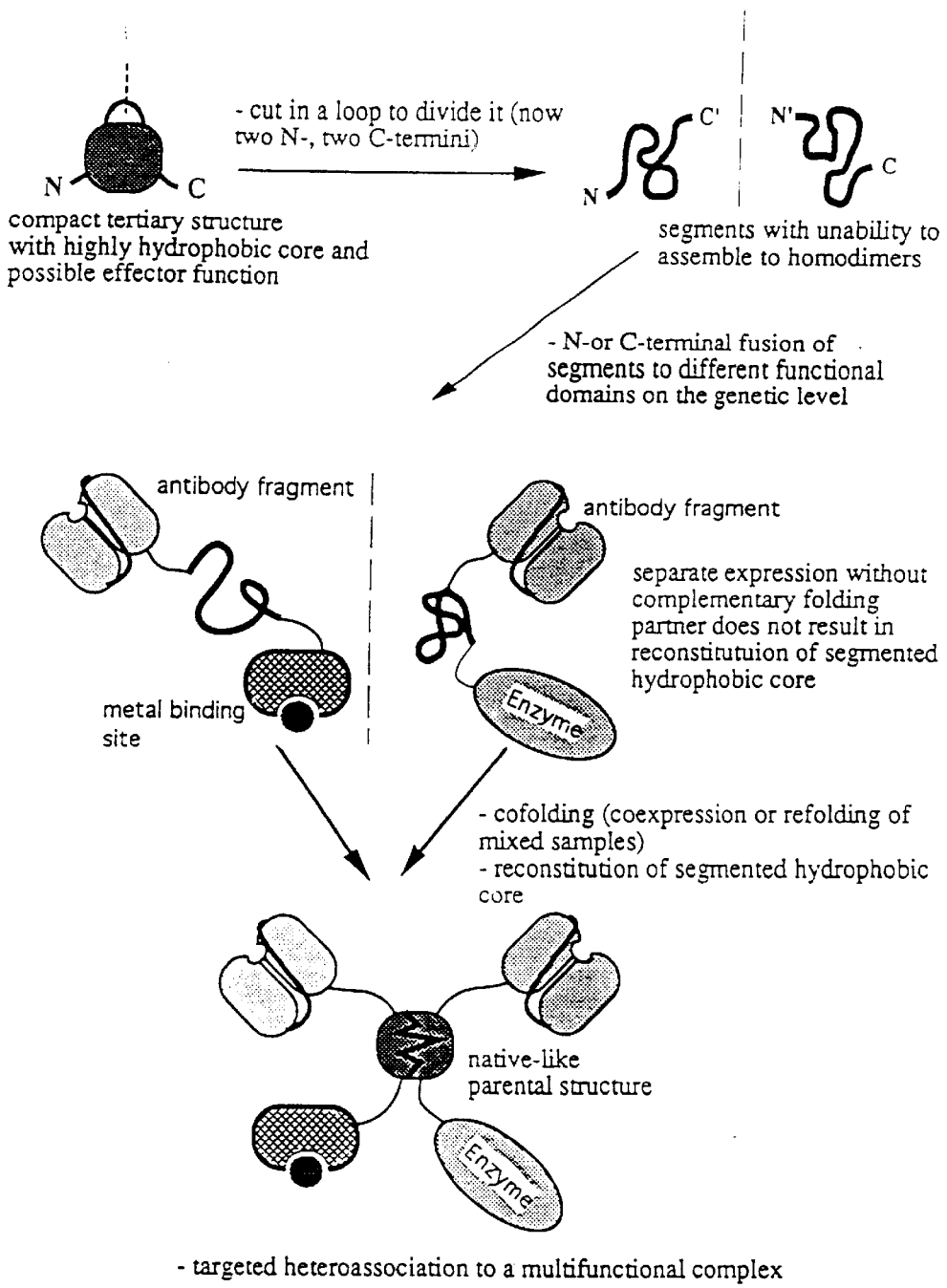
Fig. 1: schematic representation of targeted hetero-association of functional domains by fusion to a segmented tertiary structure Fig 2. Modular organization of a cistron based on a gene cassette system with unique restriction sites

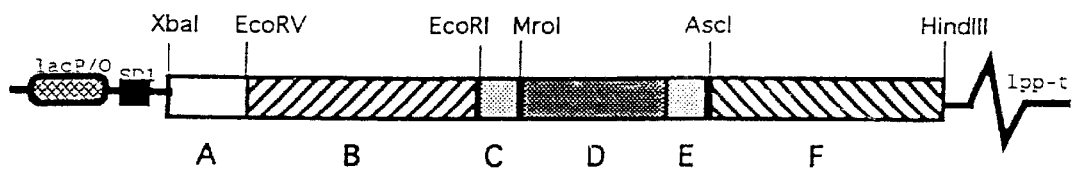

lac P/O: lac promotor/operator
SD: Shine-Dalgarno sequence
lpp-t: lpp-terminator A: optional signal sequence (ompA, phoA)
B: N-terminal functional domain (enzyme, metal binding site, antibody fragment, toxin, peptide)
C: flexible peptide linker
D: segment of assembly device
E: flexible peptide linker
F: C-terminal functional domain (enzyme, metal binding site, antibody fragment, toxin, peptide)

Fig. 3 : protein sequence of human ubiquitin (segmented after Gly35)

```
1         10          20          30      ⤴  40          50
MQIFVKTLTG KTITLEVEPS DTIENVKAKI QDKEGIPPDQ QRLIFAGKQL 60          70
EDGRTLSDYN IQKESTLHLV LRLRGG**
```

Fig. 4: MroI-Hind III gene cassette encoding for segment ALPHA of ubiquitin

```
MroI
    S   G   M   Q   I   F   V   K   T   L   T   G   K   T   I   T   L   E
   TCC GGA ATG CAG ATC TTC GTT AAA ACC CTG ACC GGT AAA ACC ATC ACC CTG GAA
            9          18          27          36          45          54
   AGG CCT TAC GTC TAG AAG CAA TTT TGG GAC TGG CCA TTT TGG TAG TGG GAC CTT

V   E   P   S   D   T   I   E   N   V   K   A   K   I   Q   D   K   E
   GTT GAA CCG TCT GAC ACC ATC GAA AAC GTT AAA GCT AAA ATC CAG GAC AAA GAA
            63          72          81          90          99         108
   CAA CTT GGC AGA CTG TGG TAG CTT TTG CAA TTT CGA TTT TAG GTC CTG TTT CTT

HindIII
    G   *   *   A
   GGT TGA TAA GCT T 3'
           117
   CCA ACT ATT CGA A 5'
```

Fig. 5: MroI-Hind III gene cassette encoding for segment BETA of ubiquitin

```
    MroI
     S   G   I   P   P   D   Q   Q   R   L   I   F   A   G   R   Q   L   E
    TCC GGA ATC CCG CCG GAC CAG CAG CGT CTG ATC TTC GCT GGT CGT CAG CTG GAA
             9          18          27          36          45          54
    AGG CCT TAG GGC GGC CTG GTC GTC GCA GAC TAG AAG CGA CCA GCA GTC GAC CTT

D   G   R   T   L   S   D   Y   N   I   Q   K   E   S   T   L   H   L
    GAC GGT CGT ACC CTG TCT GAC TAC AAC ATC CAG AAA GAA TCT ACC CTG CAC CTG
             63          72          81          90          99         108
    CTG CCA GCA TGG GAC AGA CTG ATG TTG TAG GTC TTT CTT AGA TGG GAC GTG GAC

HindIII
     V   L   R   L   *   *
    GTT CTG CGT CTG TGA TAA  3'
            117         126
    CAA GAC GCA GAC ACT ATT  5'
```

Fig. 6: EcoRI-MroI gene cassette encoding a flexible linker (huIgG3)

```
        EcoRI                                          MroI
         E   F   T   P   L   G   D   T   T   H   T   S   G
    5'  GAA TTC ACC CCG CTG GGT GAC ACC ACC CAC ACC TCC GGA  3'
                 9          18          27          36
    3'  CTT AAG TGG GGC GAC CCA CTG TGG TGG GTG TGG AGG CCT  5'
```

Fig. 7 : Construction of a monocistronic expression vector encoding a functional protein (McPC603 scFv), a flexible linker (huIgG3) and the assembly segment (ALPHA of human ubiquitin)
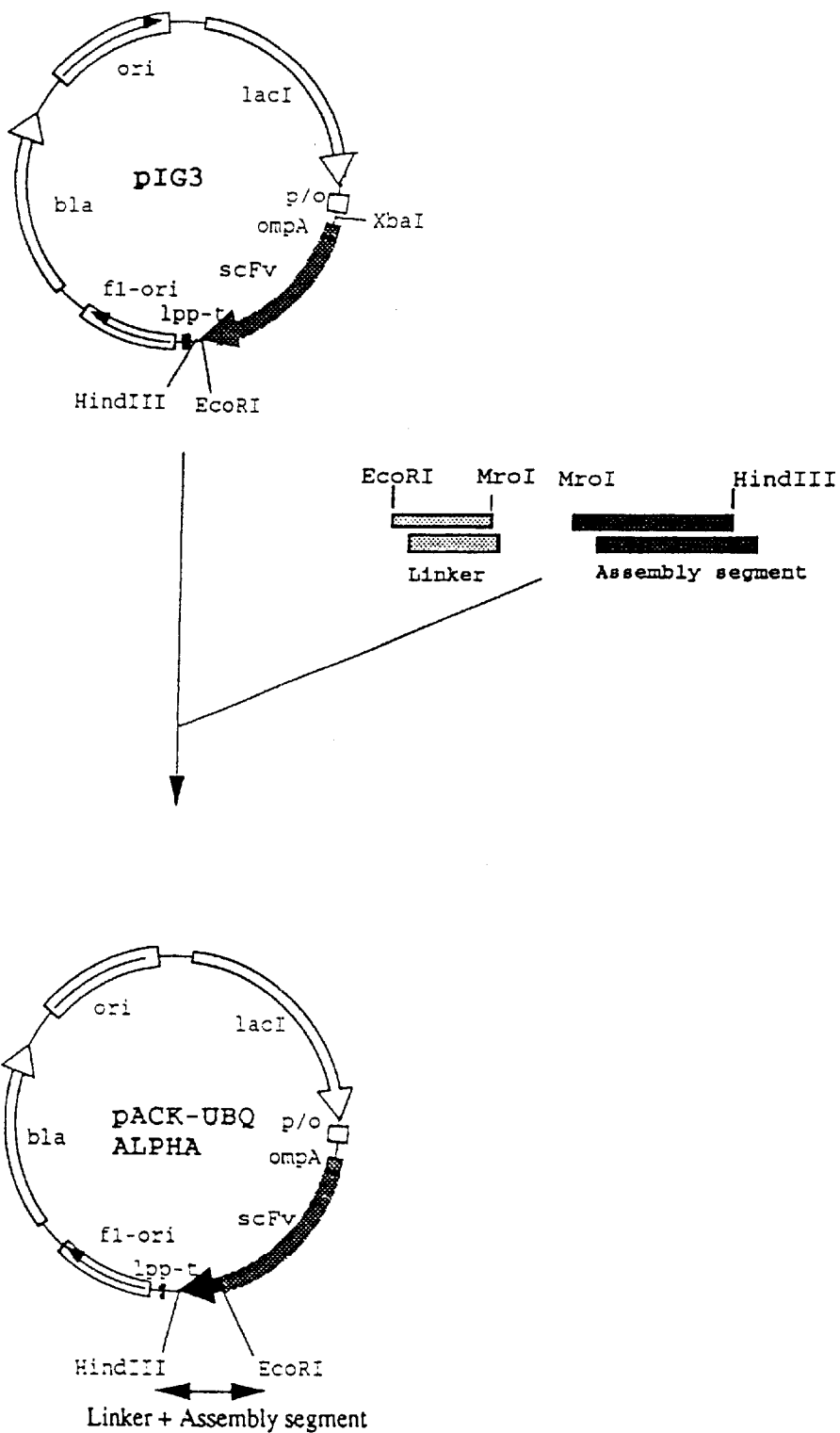

Fig. 8 : Construction of a dicistronic expression vector encoding two functional proteins (McPC603 scFv; 2H10 scFv), flexible linker (huIgG3) and the two assembly segments ALPHA and BETA of human ubiquitin.
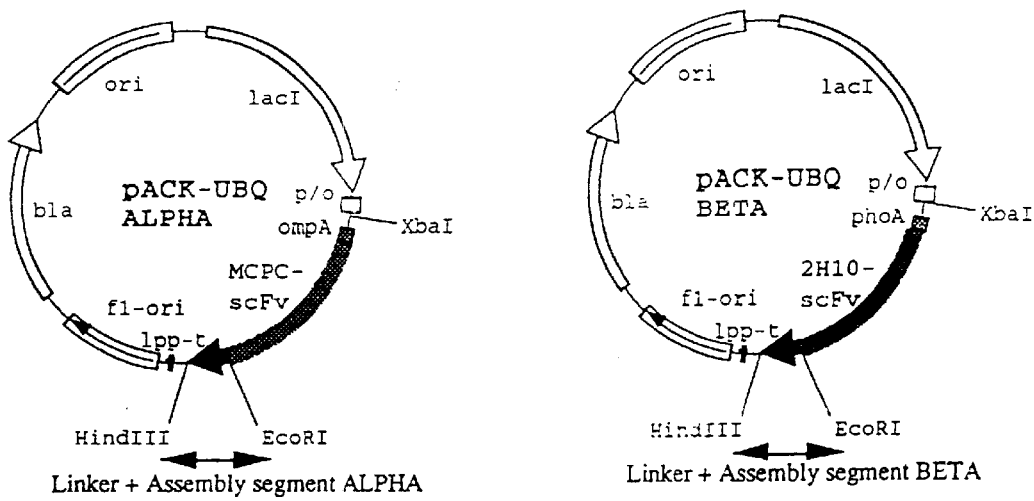
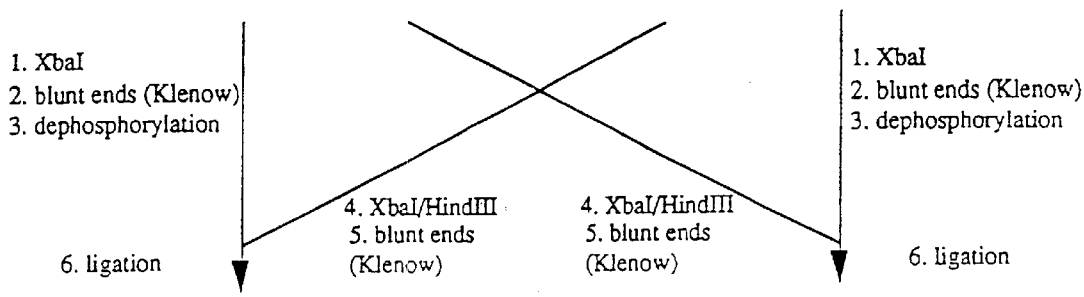
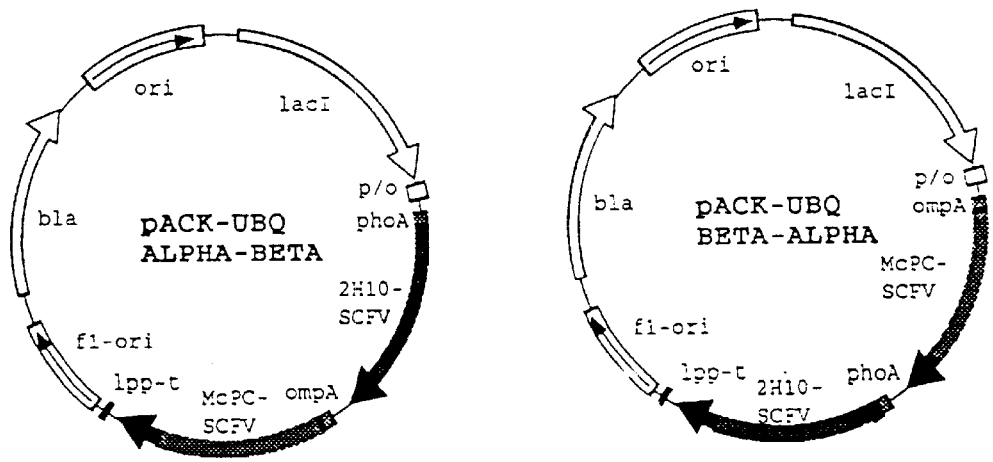

Fig. 9 : protein sequence of human ubiquitin with intersegmental disufides Cys4 and Cys66 (segmented after Gly35)

```
1         10        20         30      ⤴  40        50
MQICVKTLTG KTITLEVEPS DTIENVKAKI QDKEGIPPDQ QRLIFAGKQL 60        70
EDGRTLSDYN IQKESCLHLV LRLRGG**
```

Fig. 10: MroI-Hind III gene cassette encoding for segment ALPHA-CYS4 of ubiquitin

```
MroI
 S   G   M   Q   I   C   V   K   T   L   T   G   K   T   I   T   L   E
TCC GGA ATG CAG ATC TGC GTT AAA ACC CTG ACC GGT AAA ACC ATC ACC CTG GAA
         9          18          27          36          45          54
AGG CCT TAC GTC TAG ACG CAA TTT TGG GAC TGG CCA TTT TGG TAG TGG GAC CTT

V   E   P   S   D   T   I   E   N   V   K   A   K   I   Q   D   K   E
GTT GAA CCG TCT GAC ACC ATC GAA AAC GTT AAA GCT AAA ATC CAG GAC AAA GAA
         63          72          81          90          99         108
CAA CTT GGC AGA CTG TGG TAG CTT TTG CAA TTT CGA TTT TAG GTC CTG TTT CTT

HindIII
 G   *   *   A
GGT TGA TAA GCT T 3'
         117
CCA ACT ATT CGA A 5'
```

Fig. 11 : MroI-AscI-Hind III gene cassette encoding for segment BETA-CYS66 with C-terminal GGSGGAP linker of ubiquitin MroI
```
      S   G   I   P   P   D   Q   Q   R   L   I   F   A   G   R   Q   L   E
      TCC GGA ATC CCG CCG GAC CAG CAG CGT CTG ATC TTC GCT GGT CGT CAG CTG GAA
              9           18          27          36          45          54
      AGG CCT TAG GGC GGC CTG GTC GTC GCA GAC TAG AAG CGA CCA GCA GTC GAC CTT D   G   R   T   L   S   D   Y   N   I   Q   K   E   S   C   L   H   L
      GAC GGT CGT ACC CTG TCT GAC TAC AAC ATC CAG AAA GAA TCT TGC CTG CAC CTG
              63          72          81          90          99         108
      CTG CCA GCA TGG GAC AGA CTG ATG TTG TAG GTC TTT CTT AGA ACG GAC GTG GAC AscI         HindIII
      V   L   R   L   G   G   S   G   G   A   P   *   *
      GTT CTG CGT CTG GGG GGG AGC GGA GGC GCG CCG TGA TAA  3'
              117         126
      CAA GAC GCA GAC CCC CCC TCG CCT CCG CGC GGC ACT ATT  5'
```

Fig. 12: Protein sequence of human IL-2 (segmented after His79)

```
         10         20         30         40         50         60
    APTSSSTKKT QLQLEHLLLD LQMILNGINN YKNPKLTRML TFKFYMPKKA TELKHLQCLE

70         ↲         90        100        110        120
    EELKPLEEVL NLAQSKNFHL RPRDLISNIN VIVLELKGSE TTFMCEYADE TATIVEFLNR

130
    WITFCQSIIS TLT
```

Fig.13 : MroI-AscI-Hind III gene cassette encoding for segment ALPHA of human IL-2

```
MroI

Fig. 14 : MroI-AscI-Hind III gene cassette encoding for segment BETA of human IL-2

```
MroI
  S   G   L   R   P   R   D   L   I   S   N   I   N   V   I   V   L   E
5'TCC GGA TTA AGA CCC AGG GAC TTA ATC AGC AAT ATC AAC GTA ATA GTT CTG GAA
          9           18          27          36          45          54
  AGG CCT AAT TCT GGG TCC CTG AAT TAG TCG TTA TAG TTG CAT TAT CAA GAC CTT

L   K   G   S   E   T   T   F   M   C   E   Y   A   D   E   T   A   T
  CTA AAG GGA TCT GAA ACA ACA TTC ATG TGT GAA TAT GCT GAT GAG ACA GCA ACC
          63          72          81          90          99          108
  GAT TTC CCT AGA CTT TGT TGT AAG TAC ACA CTT ATA CGA CTA CTC TGT CGT TGG

I   V   E   F   L   N   R   W   I   T   F   C   Q   S   I   I   S   T
  ATT GTA GAA TTT CTG AAC AGA TGG ATT ACC TTT TGT CAA AGC ATC ATC TCA ACA
          117         126         135         144         153         162
  TAA CAT CTT AAA GAC TTG TCT ACC TAA TGG AAA ACA GTT TCG TAG TAG AGT TGT

AscI        HindIII
  L   T   G   G   S   G   G   A   P   *
  CTG ACT GGG GGG AGC GGA GGC GCG CCG TGA T 3'
          171         180         189
  GAC TGA CCC CCC TCG CCT CCG CGC GGC ACT A 5'
```

Fig. 15 Protein sequence of human apomyoglobin (cut after Lys47 and Lys98)

mglsdgewql vlnvwgkvea dipghgqevl irlfkghpet lekfdkfkhl ✂

51
ksedemkase dlkkhgatvl talggilkkk ghheaeikpl aqshatkhki ✂

101
pvkylefise ciiqvlqskh pgdfgadaeg amnkalelfr kdmasnykel 151
gfqg

Fig. 16 : MroI-AscI-Hind III gene cassette encoding for segment ALPHA of human apomyoglobin

```
MroI
  S   G   M   G   L   S   D   G   E   W   Q   L   V   L   N   V   W   G
 TCC GGA ATG GGT CTG TCT GAC GGT GAA TGG CAG CTG GTT CTG AAC GTT TGG GGT
          9          18          27          36          45          54
 AGG CCT TAC CCA GAC AGA CTG CCA CTT ACC GTC GAC CAA GAC TTG CAA ACC CCA

K   V   E   A   D   I   P   G   H   G   Q   E   V   L   I   R   L   F
 AAA GTT GAA GCT GAC ATC CCG GGT CAC GGT CAG GAA GTT CTG ATC CGT CTG TTC
          63          72          81          90          99         108
 TTT CAA CTT CGA CTG TAG GGC CCA GTG CCA GTC CTT CAA GAC TAG GCA GAC AAG

K   G   H   P   E   T   L   E   K   F   D   K   F   K   G   G   S   G
 AAA GGT CAC CCG GAA ACC CTG GAA AAA TTC GAC AAA TTC AAA GGG GGG AGC GGA
         117         126         135         144         153         162
 TTT CCA GTG GGC CTT TGG GAC CTT TTT AAG CTG TTT AAG TTT CCC CCC TCG CCT

AscI        HindIII
   G    A    P    *
  GGC  GCG  CCG  TGA  T 3'
                171
  CCG  CGC  GGC  ACT  A 5'
```

Fig. 17: MroI-AscI-Hind III gene cassette encoding for segment BETA of human apomyoglobin

```
MroI
  S   G   H   L   K   S   E   D   E   M   K   A   S   E   D   L   K   K
  TCC GGA CAC CTG AAA TCT GAA GAC GAA ATG AAA GCA TCT GAA GAC CTG AAA AAA
          9           18          27          36          45          54
  AGG CCT GTG GAC TTT AGA CTT CTG CTT TAC TTT CGT AGA CTT CTG GAC TTT TTT

H   G   A   T   V   L   T   A   L   G   G   I   L   K   K   K   G   H
  CAC GGT GCT ACC GTT CTG ACC GCT CTG GGT GGT ATC CTG AAA AAA AAA GGT CAC
          63          72          81          90          99          108
  GTG CCA CGA TGG CAA GAC TGG CGA GAC CCA CCA TAG GAC TTT TTT TTT CCA GTG

H   E   A   E   I   K   P   L   A   Q   S   H   A   T   K   H   K   G
  CAC GAA GCT GAA ATC AAA CCG CTG GCT CAG TCT CAC GCT ACC AAA CAC AAA GGG
          117         126         135         144         153         162
  GTG CTT CGA CTT TAG TTT GGC GAC CGA GTC AGA GTG CGA TGG TTT GTG TTT CCC

AscI        HindIII
  G   S   G   G   A   P   *
  GGG AGC GGA GGC GCG CCG TGA T 3'
          171         180
  CCC TCG CCT CCG CGC GGC ACT A 5'
```

Fig.18: MroI-AscI-Hind III gene cassette encoding for segment GAMMA of human apomyoglobin

```
  MroI
   S   G   I   P   V   K   Y   L   E   F   I   S   E   C   I   I   Q   V
  TCC GGA ATC CCG GTT AAA TAC CTG GAG TTC ATC TCT GAA TGC ATC ATC CAG GTT
           9          18          27          36          45          54
  AGG CCT TAG GGC CAA TTT ATG GAC CTC AAG TAG AGA CTT ACG TAG TAG GTC CAA

L   Q   S   K   H   P   G   D   F   G   A   D   A   E   G   A   M   N
  CTG CAG TCT AAA CAC CCG GGT GAC TTC GGT GCT GAC GCT GAA GGT GCT ATG AAC
           63          72          81          90          99         108
  GAC GTC AGA TTT GTG GGC CCA CTG AAG CCA CGA CTG CGA CTT CCA CGA TAC TTG

K   A   L   E   L   F   R   K   D   M   A   S   N   Y   K   E   L   G
  AAA GCT CTG GAA CTG TTC CGT AAA GAC ATG GCT TCT AAC TAC AAA GAA CTG GGT
          117         126         135         144         153         162
  TTT CGA GAC CTT GAC AAG GCA TTT CTG TAC CGA AGA TTG ATG TTT CTT GAC CCA
   F   S   Q   F   Q   E   T   F   V   H   S   R   V   V   F   F   Q   T
                                        AscI            HindIII
   F   Q   G   G   G   S   G   G   A   P   *
  TTC CAG GGT GGG GGG AGC GGA GGC GCG CCG TGA T 3'
          171         180         189
  AAG GTC CCA CCC CCC TCG CCT CCG CGC GGC ACT A 5'
```

Fig. 19: Peptide sequence of an endotoxin-neutralizing peptide as a functional domain

```
1          11
RWKVRKSFFKL Q
```

Fig. 20: N-terminal EcoRV-EcoRI cassette encoding an endotoxin-neutralizing peptide

```
     EcoRV                                                    EcoRI
     I   M   R   W   K   V   R   K   S   F   F   K   L   Q   E   F
5' ATC ATG CGT TGG AAA GTT CGT AAA TCT TTC TTC AAA CTG CAG GAA TTC 3'
             9          18          27          36          45
3' TAG TAC GCA ACC TTT CAA GCA TTT AGA AAG AAG TTT GAC GTC CTT AAG 5'
```

Fig. 21: C-terminal AscI-HindIII cassette encoding an endotoxin-neutralizing peptide

```
     AscI                                                    HindIII
     A   P   R   W   K   V   R   K   S   F   F   K   L   Q   *   *
5' GCG CCG CGT TGG AAA GTT CGT AAA TCT TTC TTC AAA CTG CAG TGA TAA 3'
             9          18          27          36          45
3' CGC GGC GCA ACC TTT CAA GCA TTT AGA AAG AAG TTT GAC GTC ACT ATT 5'
```

Fig. 22 AscI-HINDIII Gene cassette encoding a purification tail for IMAC

```
     AscI                    Hind III
     A   P   H   H   H   H   H   H   *   *
5' GCG CCG CAC CAC CAC CAC CAC CAC TGA TAA 3'
             9          18          27
3' CGC GGC GTG GTG GTG GTG GTG CAC ACT ATT 5'
```

Fig. 23  Protein sequence of the platelet aggregation inhibitor decorsin as a functional domain

```
     1          11         21         31
   APRLPQCQGD DQEKCLCNKD ECPPGQCRFP RGDADPYCE
```

Fig. 24  N-terminal EcoRV-EcoRI cassette encoding the platelet aggregation inhibitor decorsin

```
EcoRV
 D   I   A   P   R   L   P   Q   C   Q   G   D   D   Q   E   K   C   L
GAT ATC GCT CCG CGT CTG CCG CAG TGC CAG GGT GAC GAC CAG GAA AAA TGC CTG
         9          18          27          36          45          54
CTA TAG CGA GGC GCA GAC GGC GTC ACG GTC CCA CTG CTG GTC CTT TTT ACG GAC

C   N   K   D   E   C   P   P   G   Q   C   R   F   P   R   G   D   A
TGC AAC AAA GAC GAA TGC CCG CCG GGT CAG TGC CGT TTC CCG CGT GGT GAC GCT
         63          72          81          90          99         108
ACG TTG TTT CTG CTT ACG GGC GGC CCA GTC ACG GCA AAG GGC GCA CCA CTG CGA

EcoRI
 D   P   Y   C   E   F
GAC CCG TAC TGC GAA TTC  3'
         117         126
CTG GGC ATG ACG CTT AAG  5'
```

Fig. 25  C-terminal AscI-HindIII cassette encoding the platelet aggregation inhibitor decorsin

```
 AscI
 A   P   A   P   R   L   P   Q   C   Q   G   D   D   Q   E   K   C   L
GCG CCG GCT CCG CGT CTG CCG CAG TGC CAG GGT GAC GAC CAG GAA AAA TGC CTG
         12          21          30          39          48          57
CGC GGC CGA GGC GCA GAC GGC GTC ACG GTC CCA CTG CTG GTC CTT TTT ACG GAC

C   N   K   D   E   C   P   P   G   Q   C   R   F   P   R   G   D   A
TGC AAC AAA GAC GAA TGC CCG CCG GGT CAG TGC CGT TTC CCG CGT GGT GAC GCT
         66          75          84          93         102         111
ACG TTG TTT CTG CTT ACG GGC GGC CCA GTC ACG GCA AAG GGC GCA CCA CTG CGA

HindIII
 D   P   Y   C   E   *   *
GAC CCG TAC TGC GAA TGA TAA  3'
         120         129
CTG GGC ATG ACG CTT ACT ATT  5'
```

TARGETED HETERO-ASSOCIATION OF RECOMBINANT PROTEINS TO MULTI-FUNCTIONAL COMPLEXES

BACKGROUND OF THE INVENTION

Increasingly, there is a need for proteins which combine two or more functions, such as binding or catalysis, in a single structure. Typically, proteins which combine two or more functions are prepared either as fusion proteins or through chemical conjugation of the component functional domains. Both of these approaches suffer from disadvantages. Genetic "single chain" fusions suffer the disadvantages that (i) only a few (2–3) proteins can be fused (Rock et al., 1992, *Prot. Eng.* 5, 583–591), (ii) mutual interference between the component domains may hinder folding, and (iii) the size of the fusion protein may make it difficult to prepare. The alternative, chemical cross-linking in vitro following purification of independently expressed proteins, is difficult to control and invariably leads to undefined products and to a severe loss in yield of functional material.

Recently, methods for achieving non-covalent association of two or more of the same functional domains have been developed. This can be achieved through the use of domains attached to peptides which self-associate to form homo-multimers (Pack & Plückthun, 1992, *Biochemistry* 31, 1579–1584). For example, the association of two separately expressed scFv antibody fragments by C-terminally fused amphipathic helices in vivo provides homo-dimers of antibody fragments in *E. coli* (PCT/EP93/00082; Pack et al., 1993, *Bio/Technology* 11, 1271–1277) or homo-tetramers; (Pack et al., 1995, *J. Mol. Biol.*, 246, 28–34).

To assemble distinct protein functions such as two antibody fragments with different specificities fused to such association domains, the helices must have a tendency to form hetero-multimers. In principle, this could be achieved with complementary helices such as the hetero-dimerizing JUN and FOS zippers of the AP-1 transcription factor (O'Shea et al, 1992, *Cell* 68, 699–708). The clear disadvantage of association domains based on hetero-associated helices, however, is their pseudo-symmetry and their similar periodicity of hydrophobic and hydrophilic residues. This structural similarity results in a strong tendency to form homo-dimers and, thus, to lower significantly the yield of hetero-dimers (O'Shea et al., 1993, *Cell* 68, 699–708; Pack, 1994, Ph. D. thesis, Ludwig-Maximilians-Universität München). Furthermore, the formation of JUN/FOS hetero-dimers is kinetically disfavoured and requires a temperature-dependent unfolding of the kinetically favoured homo-dimers, especially JUN/JUN homo-dimers (PCT/EP93/00082; O'Shea et al., 1992, *Cell* 68, 699–708; Pack, 1994, Ph. D. thesis, Ludwig-Maximilians-Universität München). Because of the need of additional purification steps to separate the unwanted homo-dimers from hetero-dimers and the resulting decrease in yield, hetero-association domains based on amphipathic helices do not result in practical advantages compared to conventional chemical coupling.

These disadvantages of the prior art are overcome by the present invention which provides multi-functional polypeptides and methods for the preparation of these multi-functional proteins. This is achieved via the use of association domains which are designed to associate predominantly in a complementary fashion, and not to self-associate.

DETAILED DESCRIPTION OF THE INVENTION

In the earliest steps of protein folding, peptide chains form a disordered hydrophobic core by collapsing hydrophobic residues into the interior of an intermediate "molten globule". This hydrophobic effect is considered to be the most important driving force of folding (Matthews, 1993, *Annu. Rev. Biochem.* 62, 652–683; Fersht, 1993, *FEBS Letters* 325, 5–16). The burial of hydrophobic residues and the resulting exclusion of solvent is the determining factor in the stability of compact tertiary structures such as acyl-phosphatase (Pastore et al, *J. Mol. Biol.* 224, 427–440, 1992) interleukin-2 (Brandhuber et al., 1987, *Science* 238, 1707–1709), calbindin (Parmentier, 1990, *Adv. Exp. Med. Biol.* 269, 27–34) or ubiquitin (Briggs & Roder, 1992, *Proc. Natl. Acad. Sci. USA* 89, 2017–2021).

This concept forms the basis of the present invention, which provides individually encoded peptides or "segments" which, in a single continuous chain, would comprise a compact tertiary structure with a highly hydrophobic core. The component peptides are chosen so as to be asymmetric in their assumed structure, so as not to self-associate to form homo-multimers, but rather to associate in a complementary fashion, adopting a stable complex which resembles the parent tertiary structure. On the genetic level, these segments are encoded by interchangeable cassettes with suitable restriction sites. These standardized cassettes are fused C- or N-terminally to different recombinant proteins via a linker or hinge in a suitable expression vector system.

Thus, the present invention relates to a multi-functional polypeptide comprising:

(a) a first amino acid sequence attached to at least one functional domain;

(b) a second amino acid sequence attached to at least one further functional domain; and (c) optionally, further amino acid sequences each attached to at least one further functional domain;

wherein any one or more of said amino acid sequences interacts with at least one of said amino acid sequences in a complementary fashion to form a parental, native-like tertiary or optionally quaternary structure and wherein the parental, native-like tertiary or optionally quaternary structure is derived from a single parent polypeptide. In this context, the term parent polypeptide refers to a polypeptide which has a compact tertiary or quarternary structure with a hydrophobic core. The invention provides for many different parent polypeptides to be used as the basis for the association domain. Suitable polypeptides can be identified by searching for compact, single-domain proteins or protein fragments in the database of known protein structures (Protein Data Bank, PDB) and selecting structures that are stable and can be expressed at high yields in recombinant form. These structures can then be analyzed for hydrophobic sub-clusters by the method of Karpeisky and Ilyn (1992, *J. Mol. Biol.* 224, 629–638) or for structural units (such as β-elements or helical hairpin structures) by standard molecular modelling techniques. In a further embodiment, the present invention provides for multi-functional polypeptides wherein the single parent polypeptide is taken from the list ubiquitin, acyl phosphatase, IL-2, calbindin and myoglobin.

In a preferred embodiment, the present invention provides a multi-functional polypeptide comprising two or more amino acid sequences each attached to at least one functional domain, wherein any two or more of said amino acid sequences can associate in a complementary fashion to provide a parental, native like, tertiary or optionally quaternary structure.

The structure of the multifunctional complex of the present invention is described schematically in FIG. 1.

Polypeptide segments which do not have the ability to assemble as homodimers are derived by cutting a parental polypeptide which has a compact tertiary structure and a highly hydrophobic core. These polypeptide segments can then fused to one or more different functional domains at the genetic level. These distinct polypeptide segments which are now fused to one or more functional domains can be, for example, coexpressed resulting in the formation of a native like parental structure attached to functional domains. This parental structure is formed by the dimerization of the polypeptide segments which were derived from the original parental polypeptide. The resulting multifunctional complex, as pictured in FIG. 1, would appear as a compact tertiary structure attached to the one or more functional domains.

Once structural sub-domains are identified, the protein is dissected in such a way these sub-domains remain intact. The selection process can be expanded to proteins for which no structure is available but which satisfy the criteria of stability and good expression. For these proteins, folding sub-domains can be determined by hydrogen exchange pulse-labelling of backbone amides during the folding reaction, followed by NMR detection in the native state (Roder et al., 1988, *Nature* 355, 700–704; Udgaonkar & Baldwin, 1988, *Science* 255, 594–597). Alternatively, folding sub-domains can be identified by mild proteolysis, denaturation, purification of fragments and reconstitution in vitro (Tasayco & Carey, 1992, *Science* 255, 594–597; Wu et al., 1993, *Biochemistry* 32, 10271–10276). Finally, additional clues for the choice of cleavage sites can be obtained from the exon structure in the case of eukaryotic proteins, since the exons frequently (though not always) correspond to structural sub-domains of a protein. This has, for example, been discussed for the case of myoglobin (Go 1981, *Nature* 291, 90).

The yield of properly assembled molecules is expected to decrease significantly for constructs in which a protein domain is divided into three or more parts. This is due to the fact that several sub-domains must come together simultaneously to form a viable structure. This effect is countered by dividing the polypeptide chain into sub-domains that represent folding units (identified by the methods described above). Thus, not only the final, assembled complex but also assembly intermediates will have the stability necessary to allow their accumulation in the host during expression, resulting in a greatly improved kinetic behaviour of the system.

In solution, the isolated segments have little secondary structure and remain monomeric or form transient, non-specific and easily disrupted aggregates. Only upon mixing, either by separate expression and purification, or by co-expression, can the concerted folding of complementary segments provide the necessary intermediate interaction of residues (Matthews, 1993, *Annu. Rev. Biochem.* 62, 653–683) that results in the formation of a compact, native-like structure. This association, mainly driven by the burial of hydrophobic residues of all segments into a single hydrophobic core, leads to a targeted assembly of the N- or C-terminally fused proteins to a multi-functional complex in vivo or in vitro.

Optionally, the reconstituted native-like structure may also contribute an enzymatic or binding activity to increase the number of effector functions in the assembled complex. Accordingly, the present invention also provides a multi-functional polypeptide as described above, in which the native-like, tertiary or quaternary structure provides a biological activity. For example, when acyl phosphatase is used as the basis of the association domain, it is expected that the multi-functional polypeptide will retain some phosphatase activity.

The present invention provides for many different types of functional domains to be linked into the multi-functional polypeptide. Particularly preferred are cases in which one or more, preferably two, of said functional domains are fragments derived from molecules of the immunoglobulin superfamily. In particularly preferred embodiments, said fragments are antibody fragments. Also preferred are cases in which at least one of the functional domains possesses biological activity other than that associated with a fragment derived from a member of the immunoglobulin superfamily. By way of example, the present invention provides for the targeted assembly of enzymes, toxins, cytokines, peptide hormones, immunoglobulins, metal binding domains, soluble receptors, lectins, lipoproteins, purification tails and bioactive peptides to multi-functional complexes (FIG. 1) based on a modular system of expression vectors, restriction sites and "plug-in" gene cassettes coding for assembly segments, peptide linkers and functional domains (FIG. 2).

If covalent linkage between the segments is necessary to prevent dissociation at low concentrations, cysteines can be introduced to form inter-segmental disulphide bridges between the amino acid sequences which comprise the association domain (Ecker et al., 1989, *J. Biol. Chem.* 264, 1887–1893; Pack & Plückthun, 1992, *Biochemistry* 31, 1579–1584). Accordingly, the present invention provides multi-functional polypeptides wherein the folding of the component amino acid sequences is stabilized by a covalent bond.

In order to provide some flexibility between the association domain and the appended functional domains, it may be desired to incorporate a linker peptide. Accordingly, the present invention provides for multi-functional polypeptides of the type described above wherein at least one of the functional domains is coupled to said amino acid sequence via a flexible peptide linker. By way of example, the flexible linker may be derived from the hinge region of an antibody.

The invention enables even more complex multi-functional polypeptides to be constructed via the attachment of at least one further (poly)peptide to one or more of said amino acid sequences. By way of example, the further (poly)peptide can be taken from the list enzymes, toxins, cytokines, peptide hormones, immunoglobulins, metal binding domains, soluble receptors, lectins, lipoproteins, purification tails, in particular peptides which are able to bind to an independent binding entity, bioactive peptides, preferably of 5 to 15 amino acid residues, metal binding proteins, DNA binding domains, transcription factors and growth factors.

For therapeutic purposes, it is often desirable that proteinaceous substances display the minimum possible immunogenicity. Accordingly, the present invention provides for multi-functional polypeptides as described above in which at least one of said amino acid sequences, functional domains, or further (poly)peptides is of human origin.

In addition to the peptides and proteins provided above, the present invention also provides for DNA sequences, vectors, preferably bicistronic vectors, vector cassettes, characterised in that they comprise a DNA sequence encoding an amino acid sequence and optionally at least one further (poly)peptide comprised in the multifunctional polypeptide of the invention, and additionally at least one, preferably singular cloning sites for inserting the DNA encoding at least one further functional domain or that they comprise DNA sequences encoding the amino acid sequences, and optionally the further (poly)peptide(s) comprised in the multifunctional polypeptide of the invention and suitable restriction sites for the cloning of DNA sequences encoding the functional domains, such that upon expression of the DNA sequences after the insertion of the DNA sequences encoding the functional domains into said restriction sites, in a suitable host the multifunctional polypeptide of the invention is formed. In a preferred embodiment said vector cassette is characterised in that it comprises the inserted DNA sequence(s) encoding said functional domain(s) and host cells transformed with at least one vector or vector cassette of the invention which can be used for the preparation of said multi-functional polypeptides.

In a further preferred embodiment, said host cell is a mammalian, preferably human, yeast, insect, plant or bacterial, preferably E. coli cell.

The invention further provides for a method for the production of a multifunctional polypeptide of the invention, which comprises culturing the host cell of the invention in a suitable medium, and recovering said multifunctional polypeptide produced by said host cell.

In a further embodiment, the invention relates to a method for the production of a multifunctional polypeptide of the invention which comprises culturing at least two host cells of the invention in a suitable medium, said host cells each producing only one of said first and said second amino acid sequences attached to at least one further functional domain, recovering the amino acid sequences, mixing thereof under mildly denaturing conditions and allowing in vitro folding of the multifunctional polypeptide of the invention from said amino acid sequences.

In a particular preferred embodiment, said method is characterised in that the further amino acid sequences attached to at least one further functional domain are/is produced by at least one further host cell not producing said first or second amino acid sequence.

In another particularly preferred embodiment of the invention, said method is characterised in that at least one further amino acid sequence attached to at least one further functional domain is produced by the host cell of the invention producing said first or second amino acid sequence.

In further preferred embodiments, the present invention provides for pharmaceutical and diagnostic compositions comprising the multi-functional polypeptides described above, said pharmaceutical compositions optionally comprising a pharmaceutically acceptable carrier. Finally, the invention provides for a kit comprising one or more vector cassettes useful in the preparation of said multi-functional polypeptides.

The invention is now illustrated by reference to the following examples, which are provided for the purposes of illustration only and are not intended to limit the scope of the invention.

EXAMPLE 1

Segmented Human Ubiquitin as an Assembly Device

Ubiquitin is a compact intracellular protein of only 76 residues (FIG. 3) and a molecular weight of 5 kDa. It shows the highest conservation among all known proteins and is involved in the degradation pathway of intracellular eukaryotic proteins by forming intermediate isopeptide bonds to its C-terminus and to Lys48 (Hershko & Ciechanover, 1992, Ann. Rev. Biochem. 61, 761–807).

To use ubiquitin as an assembly device, the unwanted function can be abolished by truncation of the last three C-terminal residues (—Arg-Gly-Gly), and the exchange of Lys48 to Arg, which prevents the formation of isopeptide bonds to this residue. The altered sequence is then divided in a loop at position Gly36, so that the hydrophobic core falls apart into two segments (called ALPHA and BETA). The synthetic nucleotide sequence of the segments (FIGS. 4, 5) carry appropriate restriction sites (MroI-HindIII) at the termini, so that the cassette encoding the segments can be easily ligated to a EcoRI-MroI cassette encoding the flexible linker (hinge of huIgG3; FIG. 6). The cassettes are inserted into the expression vector pIG3 (EcoRI-HindIII; FIG. 7) encoding the scFv fragment of the antibody McPC603 under the lac promoter/operator (Ge et al., 1995, in: *Antibody engineering: A practical approach*. IRL Press, New York, Borrebaeck ed., 229–261). Insertion of a second functional fragment (scFv fragment of the anti-β-lactam antibody 2H10 with phoA signal sequence) linked to association segment BETA as an XbaI-HindIII DNA fragment (FIG. 8) results in a di-cistronic expression vector (Pack, 1994, Ph. D. thesis, Ludwig-Maximilians-Universität München). After induction with IPTG and translation, the signal sequences guide the antibody fragments fused to the assembly segments to the periplasm, where they assemble to a complex with a reconstituted native-like ubiquitin fold and two different antibody specificities. The complex, a bispecific immunoglobulin, can be recovered and purified by affinity chromatography of cell extract (Pack, 1994, Ph. D. thesis, Ludwig-Maximilians-Universität München).

EXAMPLE 2

Covalent Linkage of the Native-Like Tertiary Structure of the Assembly Device by Engineered Disulphide Bridges and Combination of a C-Terminal Peptide Linker with an In-Frame Restriction Site The conformational stability of undivided, native ubiquitin can be enhanced by introduction of disulfides at positions 4 and 66 without perturbation in the backbone (Ecker et al., 1989, *J. Biol. Chem.* 264, 1887–1893; FIG. 9). In the context of this invention, the engineering of disulfide bridges provides the covalent linkage of segments (FIGS. 10, 11) after co-folding and assembly.

To raise the number of possible functional domains in the assembled complex, a C-terminal peptide can be fused to one or more of the segments of the assembly device. To fuse a functional domain like an enzyme, cytokine, antibody fragment, purification peptide or toxin to this linker, a restriction site, preferably unique, has to be introduced in-frame (FIG. 11). Gene synthesis, cloning, expression as well as recovery of the assembled, covalently linked complex is according to example 1.

EXAMPLE 3

Segmented Human Interleukin-2 (IL2) as an Assembly Device

Human Interleukin-2 (Brandhuber et al., 1987, *Science* 238, 1707–1709; Kuziel & Greene, 1991, in: *The Cytokine Handbook. Academic Press*. 84–100) is used as an assembly device by segmentation between position His79 and Lys 80 (FIG. 12). The device, encoded by MroI-AscI-HindIII gene cassettes (FIGS. 13, 14) combines the low immunogenicity of the plasmatic protein with a preferable effector function of the native-like cytokine structure and an inter-segmental cysteine bridge (Cys58–Cys105) after assembly. The combination of one or more antibody fragments against tumor antigens with additional cytokines like IL6 or IL 12 targets the multi-cytokine complex (Rock et al., 1992, *Prot. Eng.* 5, 583–591) directly to the tumour.

EXAMPLE 4

Segmented Human Apomyoglobin as an Assembly Device with Three Segments

To use more than two segments of a native structure as an assembly device, the hydrophobic interface between the segments has to be large enough to provide the sufficient hydrophobic interaction for non-covalent linkage. Myoglobin (FIG. 15) is expressible in large amounts in *E. coli* (Guillemette et al., 1991, *Protein Eng.* 4, 585–592). Up to six functional domains can be assembled by a threefold segmented structure (FIGS. 16, 17, 18), three at the N-termini and three at the C-termini of the segments. The presence of heme additionally stabilizes the native-like apomyoglobin fold and can be used as a switch to influence the association constant of the multi-functional complex.

EXAMPLE 5

Bioactive Peptides as Functional Domains

Certain peptides derived from amphipathic loop structures of LPS-binding proteins (Hoess et al., 1993, *EMBO J.* 12, 3351–3356) are able to neutralize endotoxin. This effect is enhanced by multivalent display of these short peptides (10–15 residues; Hoess, unpublished results). The present invention provides a method to express and assemble several of short peptides (FIG. 19), fused to an assembly segment, in a multivalent complex or in combination with other functional domains. The peptides can be fused either to the N-or to the C-terminus (FIGS. 20, 21) of the assembly domain via the peptide linkers.

EXAMPLE 16

A Purification Tail for IMAC as a Functional Domain

Peptide tails consisting of histidines are able to coordinate metal ions. They are used for purification of native proteins in immobilized metal affinity chromatography (IMAC). Multivalent display of the purification tail considerably improves the maximum purity achievable by IMAC (Lindner et al., 1992, *Methods: a companion to methods in enzymology* 4, 41–56). One or more gene cassettes (FIG. 22) encoding a polyhistidine tail can be fused to the assembly segment to provide a simple and efficient purification method for multi-functional complexes.

EXAMPLE 7

The Platelet Aggregation Inhibitor Decorsin as a Functional Domain

Decorsin, a 39 residue protein of the leech *Macrobdella decora* (FIG. 23), acts as a potent antagonist of the platelet glycoprotein IIb-IIIa (Seymour et al., 1990, *J. Biol. Chem.* 265, 10143–10147). The gene cassette encoding the decorsin can be fused C- or N-terminally to an association segment (FIGS. 24, 25). In arterial thrombotic deseases, a multivalent decorsin complex combined with an anti-fibrin antibody fragment can act as a powerful antithrombotic agent.

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 76 amino acids
      (B) TYPE: amino acid
      (C) STRANDEDNESS: <Unknown>
      (D) TOPOLOGY: linear (ii) MOLECULE TYPE: protein (vi) ORIGINAL SOURCE:
      (A) ORGANISM: Homo sapiens (xi) SEQUENCE DESCRIPTION: SEQ ID NO: 1:

```
Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

(2) INFORMATION FOR SEQ ID NO: 2:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..111
        (D) OTHER INFORMATION: /product= "segment ALPHA of
            ubiquitin"

(xi) SEQUENCE DESCRIPTION: SEQ ID NO: 2:

```
TCC GGA ATG CAG ATC TTC GTT AAA ACC CTG ACC GGT AAA ACC ATC ACC        48
Ser Gly Met Gln Ile Phe Val Lys Thr Leu Thr Gly Lys Thr Ile Thr
 1               5                  10                  15

CTG GAA GTT GAA CCG TCT GAC ACC ATC GAA AAC GTT AAA GCT AAA ATC        96
Leu Glu Val Glu Pro Ser Asp Thr Ile Glu Asn Val Lys Ala Lys Ile
            20                  25                  30

CAG GAC AAA GAA GGT TGATAAGCTT                                        121
Gln Asp Lys Glu Gly
        35
```

(2) INFORMATION FOR SEQ ID NO: 3:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO: 3:

```
Ser Gly Met Gln Ile Phe Val Lys Thr Leu Thr Gly Lys Thr Ile Thr
 1               5                  10                  15

Leu Glu Val Glu Pro Ser Asp Thr Ile Glu Asn Val Lys Ala Lys Ile
            20                  25                  30

Gln Asp Lys Glu Gly
        35
```

(2) INFORMATION FOR SEQ ID NO: 4:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..120
        (D) OTHER INFORMATION: /product= "segment BETA of
            ubiquitin"

(xi) SEQUENCE DESCRIPTION: SEQ ID NO: 4:

```
TCC GGA ATC CCG CCG GAC CAG CAG CGT CTG ATC TTC GCT GGT CGT CAG        48
Ser Gly Ile Pro Pro Asp Gln Gln Arg Leu Ile Phe Ala Gly Arg Gln
 1               5                  10                  15

CTG GAA GAC GGT CGT ACC CTG TCT GAC TAC AAC ATC CAG AAA GAA TCT        96
```

```
Leu Glu Asp Gly Arg Thr Leu Ser Asp Tyr Asn Ile Gln Lys Glu Ser
        20                  25                  30
ACC CTG CAC CTG GTT CTG CGT CTG TGATAA                                126
Thr Leu His Leu Val Leu Arg Leu
        35                  40
```

(2) INFORMATION FOR SEQ ID NO: 5:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO: 5:

```
Ser Gly Ile Pro Pro Asp Gln Gln Arg Leu Ile Phe Ala Gly Arg Gln
 1               5                  10                  15
Leu Glu Asp Gly Arg Thr Leu Ser Asp Tyr Asn Ile Gln Lys Glu Ser
        20                  25                  30
Thr Leu His Leu Val Leu Arg Leu
        35                  40
```

(2) INFORMATION FOR SEQ ID NO: 6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..39
        (D) OTHER INFORMATION: /product= "flexible linker
            (huIgG3)"

(xi) SEQUENCE DESCRIPTION: SEQ ID NO: 6:

```
GAA TTC ACC CCG CTG GGT GAC ACC ACC CAC ACC TCC GGA                    39
Glu Phe Thr Pro Leu Gly Asp Thr Thr His Thr Ser Gly
 1               5                  10
```

(2) INFORMATION FOR SEQ ID NO: 7:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 7:

```
Glu Phe Thr Pro Leu Gly Asp Thr Thr His Thr Ser Gly
 1               5                  10
```

(2) INFORMATION FOR SEQ ID NO: 8:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: protein (vi) ORIGINAL SOURCE:

(A) ORGANISM: Homo sapiens (xi) SEQUENCE DESCRIPTION: SEQ ID NO: 8:

Met Gln Ile Cys Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Cys Leu His Leu Val Leu Arg Leu Arg Gly Gly
65                  70                  75

(2) INFORMATION FOR SEQ ID NO: 9:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..111
        (D) OTHER INFORMATION: /product= "segment ALPHA-CYS4 of
             ubiquitin"

(xi) SEQUENCE DESCRIPTION: SEQ ID NO: 9:

TCC GGA ATG CAG ATC TGC GTT AAA ACC CTG ACC GGT AAA ACC ATC ACC        48
Ser Gly Met Gln Ile Cys Val Lys Thr Leu Thr Gly Lys Thr Ile Thr
1               5                   10                  15

CTG GAA GTT GAA CCG TCT GAC ACC ATC GAA AAC GTT AAA GCT AAA ATC        96
Leu Glu Val Glu Pro Ser Asp Thr Ile Glu Asn Val Lys Ala Lys Ile
            20                  25                  30

CAG GAC AAA GAA GGT TGATAAGCTT                                        121
Gln Asp Lys Glu Gly
        35

(2) INFORMATION FOR SEQ ID NO: 10:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO: 10:

Ser Gly Met Gln Ile Cys Val Lys Thr Leu Thr Gly Lys Thr Ile Thr
1               5                   10                  15

Leu Glu Val Glu Pro Ser Asp Thr Ile Glu Asn Val Lys Ala Lys Ile
            20                  25                  30

Gln Asp Lys Glu Gly
        35

(2) INFORMATION FOR SEQ ID NO: 11:

(i) SEQUENCE CHARACTERISTICS:
        (A) LENGTH: 147 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..141
        (D) OTHER INFORMATION: /product= "segment of BETA-CYS66
            with c-Terminal GGSGGAP linker of ubiquitin"

(xi) SEQUENCE DESCRIPTION: SEQ ID NO: 11:

```
TCC GGA ATC CCG CCG GAC CAG CAG CGT CTG ATC TTC GCT GGT CGT CAG      48
Ser Gly Ile Pro Pro Asp Gln Gln Arg Leu Ile Phe Ala Gly Arg Gln
 1               5                  10                  15

CTG GAA GAC GGT CGT ACC CTG TCT GAC TAC AAC ATC CAG AAA GAA TCT      96
Leu Glu Asp Gly Arg Thr Leu Ser Asp Tyr Asn Ile Gln Lys Glu Ser
            20                  25                  30

TGC CTG CAC CTG GTT CTG CGT CTG GGG GGA AGC GGA GGC GCG CCG         141
Cys Leu His Leu Val Leu Arg Leu Gly Gly Ser Gly Gly Ala Pro
        35                  40                  45

TGATAA                                                              147
```

(2) INFORMATION FOR SEQ ID NO: 12:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO: 12:

```
Ser Gly Ile Pro Pro Asp Gln Gln Arg Leu Ile Phe Ala Gly Arg Gln
 1               5                  10                  15

Leu Glu Asp Gly Arg Thr Leu Ser Asp Tyr Asn Ile Gln Lys Glu Ser
            20                  25                  30

Cys Leu His Leu Val Leu Arg Leu Gly Gly Ser Gly Gly Ala Pro
        35                  40                  45
```

(2) INFORMATION FOR SEQ ID NO: 13:

(i) SEQUENCE CHARACTERISTICS:
        (A) LENGTH: 133 amino acids
        (B) TYPE: amino acid
        (C) STRANDEDNESS: <Unknown>
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 13:

```
Ala Pro Thr Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Gly Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

(2) INFORMATION FOR SEQ ID NO: 14:

(i) SEQUENCE CHARACTERISTICS:
        (A) LENGTH: 268 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..264
        (D) OTHER INFORMATION: /product= "segment ALPHA of human
            IL-2"

(xi) SEQUENCE DESCRIPTION: SEQ ID NO: 14:

```
TCC GGA GCA CCT ACT TCA AGT TCT ACA AAG AAA ACA CAG CTA CAA CTG      48
Ser Gly Ala Pro Thr Ser Ser Ser Thr Lys Lys Thr Gln Leu Gln Leu
 1               5                  10                  15

GAG CAT TTA CTG CTG GAT TTA CAG ATG ATT TTG AAT GGA ATT AAT AAT      96
Glu His Leu Leu Leu Asp Leu Gln Met Ile Leu Asn Gly Ile Asn Asn
                20                  25                  30

TAC AAG AAT CCC AAA CTC ACC AGG ATG CTC ACA TTT AAG TTT TAC ATG     144
Tyr Lys Asn Pro Lys Leu Thr Arg Met Leu Thr Phe Lys Phe Tyr Met
         35                  40                  45

CCC AAG AAG GCC ACA GAA CTG AAA CAT CTT CAG TGT CTA GAA GAA GAA     192
Pro Lys Lys Ala Thr Glu Leu Lys His Leu Gln Cys Leu Glu Glu Glu
     50                  55                  60

CTC AAA CCT CTG GAG GAA GTG CTA AAT TTA GCT CAA AGC AAA AAC TTT     240
Leu Lys Pro Leu Glu Glu Val Leu Asn Leu Ala Gln Ser Lys Asn Phe
 65                  70                  75                  80

CAC GGG GGG AGC GGA GGC GCG CCG TGAT                                268
His Gly Gly Ser Gly Gly Ala Pro
                 85
```

(2) INFORMATION FOR SEQ ID NO: 15:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO: 15:

```
Ser Gly Ala Pro Thr Ser Ser Ser Thr Lys Lys Thr Gln Leu Gln Leu
 1               5                  10                  15

Glu His Leu Leu Leu Asp Leu Gln Met Ile Leu Asn Gly Ile Asn Asn
                20                  25                  30

Tyr Lys Asn Pro Lys Leu Thr Arg Met Leu Thr Phe Lys Phe Tyr Met
         35                  40                  45

Pro Lys Lys Ala Thr Glu Leu Lys His Leu Gln Cys Leu Glu Glu Glu
     50                  55                  60
```

```
Leu Lys Pro Leu Glu Glu Val Leu Asn Leu Ala Gln Ser Lys Asn Phe
 65                  70                  75                  80

His Gly Gly Ser Gly Gly Ala Pro
                85
```

(2) INFORMATION FOR SEQ ID NO: 16:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..189
        (D) OTHER INFORMATION: /product= "segment BETA of human
            IL-2"

(xi) SEQUENCE DESCRIPTION: SEQ ID NO: 16:

```
TCC GGA TTA AGA CCC AGG GAC TTA ATC AGC AAT ATC AAC GTA ATA GTT      48
Ser Gly Leu Arg Pro Arg Asp Leu Ile Ser Asn Ile Asn Val Ile Val
 1               5                  10                  15

CTG GAA CTA AAG GGA TCT GAA ACA ACA TTC ATG TGT GAA TAT GCT GAT      96
Leu Glu Leu Lys Gly Ser Glu Thr Thr Phe Met Cys Glu Tyr Ala Asp
            20                  25                  30

GAG ACA GCA ACC ATT GTA GAA TTT CTG AAC AGA TGG ATT ACC TTT TGT     144
Glu Thr Ala Thr Ile Val Glu Phe Leu Asn Arg Trp Ile Thr Phe Cys
        35                  40                  45

CAA AGC ATC ATC TCA ACA CTG ACT GGG GGG AGC GGA GGC GCG CCG         189
Gln Ser Ile Ile Ser Thr Leu Thr Gly Gly Ser Gly Gly Ala Pro
    50                  55                  60

TGAT                                                                 193
```

(2) INFORMATION FOR SEQ ID NO: 17:

(i) SEQUENCE CHARACTERISTICS:
        (A) LENGTH: 63 amino acids
        (B) TYPE: amino acid
        (D) TOPOLOGY: linear (ii) MOLECULE TYPE: protein (xi) SEQUENCE DESCRIPTION: SEQ ID NO: 17:

```
Ser Gly Leu Arg Pro Arg Asp Leu Ile Ser Asn Ile Asn Val Ile Val
 1               5                  10                  15

Leu Glu Leu Lys Gly Ser Glu Thr Thr Phe Met Cys Glu Tyr Ala Asp
            20                  25                  30

Glu Thr Ala Thr Ile Val Glu Phe Leu Asn Arg Trp Ile Thr Phe Cys
        35                  40                  45

Gln Ser Ile Ile Ser Thr Leu Thr Gly Gly Ser Gly Gly Ala Pro
    50                  55                  60
```

(2) INFORMATION FOR SEQ ID NO: 18:

(i) SEQUENCE CHARACTERISTICS:
        (A) LENGTH: 154 amino acids
        (B) TYPE: amino acid
        (C) STRANDEDNESS: <Unknown>
        (D) TOPOLOGY: linear (ii) MOLECULE TYPE: protein (vi) ORIGINAL SOURCE:
    (A) ORGANISM: Homo sapiens (xi) SEQUENCE DESCRIPTION: SEQ ID NO: 18:

```
Met Gly Leu Ser Asp Gly Glu Trp Gln Leu Val Leu Asn Val Trp Gly
 1               5                  10                  15

Lys Val Glu Ala Asp Ile Pro Gly His Gly Gln Glu Val Leu Ile Arg
            20                  25                  30

Leu Phe Lys Gly His Pro Glu Thr Leu Glu Lys Phe Asp Lys Phe Lys
        35                  40                  45

His Leu Lys Ser Glu Asp Glu Met Lys Ala Ser Glu Asp Leu Lys Lys
 50                  55                  60

His Gly Ala Thr Val Leu Thr Ala Leu Gly Gly Ile Leu Lys Lys Lys
 65                  70                  75                  80

Gly His His Glu Ala Glu Ile Lys Pro Leu Ala Gln Ser His Ala Thr
                85                  90                  95

Lys His Lys Ile Pro Val Lys Tyr Leu Glu Phe Ile Ser Glu Cys Ile
            100                 105                 110

Ile Gln Val Leu Gln Ser Lys His Pro Gly Asp Phe Gly Ala Asp Ala
        115                 120                 125

Glu Gly Ala Met Asn Lys Ala Leu Glu Leu Phe Arg Lys Asp Met Ala
    130                 135                 140

Ser Asn Tyr Lys Glu Leu Gly Phe Gln Gly
145                 150
```

(2) INFORMATION FOR SEQ ID NO: 19:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..171
        (D) OTHER INFORMATION: /product= "segment ALPHA of human
            apomyoglobin"

(xi) SEQUENCE DESCRIPTION: SEQ ID NO: 19:

```
TCC GGA ATG GGT CTG TCT GAC GGT GAA TGG CAG CTG GTT CTG AAC GTT      48
Ser Gly Met Gly Leu Ser Asp Gly Glu Trp Gln Leu Val Leu Asn Val
 1               5                  10                  15

TGG GGT AAA GTT GAA GCT GAC ATC CCG GGT CAC GGT CAG GAA GTT CTG      96
Trp Gly Lys Val Glu Ala Asp Ile Pro Gly His Gly Gln Glu Val Leu
            20                  25                  30

ATC CGT CTG TTC AAA GGT CAC CCG GAA ACC CTG GAA AAA TTC GAC AAA     144
Ile Arg Leu Phe Lys Gly His Pro Glu Thr Leu Glu Lys Phe Asp Lys
        35                  40                  45

TTC AAA GGG GGG AGC GGA GGC GCG CCG TGAT                            175
Phe Lys Gly Gly Ser Gly Gly Ala Pro
     50                  55
```

(2) INFORMATION FOR SEQ ID NO: 20:

(i) SEQUENCE CHARACTERISTICS:
        (A) LENGTH: 57 amino acids
        (B) TYPE: amino acid
        (D) TOPOLOGY: linear (ii) MOLECULE TYPE: protein (xi) SEQUENCE DESCRIPTION: SEQ ID NO: 20:

```
Ser Gly Met Gly Leu Ser Asp Gly Glu Trp Gln Leu Val Leu Asn Val
 1               5                  10                  15

Trp Gly Lys Val Glu Ala Asp Ile Pro Gly His Gly Gln Val Leu
                20                  25                  30

Ile Arg Leu Phe Lys Gly His Pro Glu Thr Leu Glu Lys Phe Asp Lys
                35                  40                  45

Phe Lys Gly Gly Ser Gly Gly Ala Pro
                50                  55
```

(2) INFORMATION FOR SEQ ID NO: 21:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..180
        (D) OTHER INFORMATION: /product= "segment BETA of human
           apomyoglobin"

(xi) SEQUENCE DESCRIPTION: SEQ ID NO: 21:

```
TCC GGA CAC CTG AAA TCT GAA GAC GAA ATG AAA GCA TCT GAA GAC CTG         48
Ser Gly His Leu Lys Ser Glu Asp Glu Met Lys Ala Ser Glu Asp Leu
 1               5                  10                  15

AAA AAA CAC GGT GCT ACC GTT CTG ACC GCT CTG GGT GGT ATC CTG AAA         96
Lys Lys His Gly Ala Thr Val Leu Thr Ala Leu Gly Gly Ile Leu Lys
                20                  25                  30

AAA AAA GGT CAC CAC GAA GCT GAA ATC AAA CCG CTG GCT CAG TCT CAC         144
Lys Lys Gly His His Glu Ala Glu Ile Lys Pro Leu Ala Gln Ser His
                35                  40                  45

GCT ACC AAA CAC AAA GGG GGG AGC GGA GGC GCG CCG TGAT                    184
Ala Thr Lys His Lys Gly Gly Ser Gly Gly Ala Pro
                50                  55                  60
```

(2) INFORMATION FOR SEQ ID NO: 22:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 22:

```
Ser Gly His Leu Lys Ser Glu Asp Glu Met Lys Ala Ser Glu Asp Leu
 1               5                  10                  15

Lys Lys His Gly Ala Thr Val Leu Thr Ala Leu Gly Gly Ile Leu Lys
                20                  25                  30

Lys Lys Gly His His Glu Ala Glu Ile Lys Pro Leu Ala Gln Ser His
                35                  40                  45

Ala Thr Lys His Lys Gly Gly Ser Gly Gly Ala Pro
                50                  55                  60
```

(2) INFORMATION FOR SEQ ID NO: 23:

(i) SEQUENCE CHARACTERISTICS:
    (A) LENGTH: 196 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic gene"

(ix) FEATURE:
    (A) NAME/KEY: CDS
    (B) LOCATION: 1..192
    (D) OTHER INFORMATION: /product= "segment GAMMA of human
        apomyoglobin"

(xi) SEQUENCE DESCRIPTION: SEQ ID NO: 23:

```
TCC GGA ATC CCG GTT AAA TAC GTG GAG TTC ATC TCT GAA TGC ATC ATC     48
Ser Gly Ile Pro Val Lys Tyr Val Glu Phe Ile Ser Glu Cys Ile Ile
 1               5                  10                  15

CAG GTT CTG CAG TCT AAA CAC CCG GGT GAC TTC GGT GCT GAC GCT GAA     96
Gln Val Leu Gln Ser Lys His Pro Gly Asp Phe Gly Ala Asp Ala Glu
             20                  25                  30

GGT GCT ATG AAC AAA GCT CTG GAA CTG TTC CGT AAA GAC ATG GCT TCT    144
Gly Ala Met Asn Lys Ala Leu Glu Leu Phe Arg Lys Asp Met Ala Ser
         35                  40                  45

AAC TAC AAA GAA CTG GGT TTC CAG GGT GGG GGG AGC GGA GGC GCG CCG    192
Asn Tyr Lys Glu Leu Gly Phe Gln Gly Gly Gly Ser Gly Gly Ala Pro
 50                  55                  60

TGAT                                                                196
```

(2) INFORMATION FOR SEQ ID NO: 24:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 24:

```
Ser Gly Ile Pro Val Lys Tyr Val Glu Phe Ile Ser Glu Cys Ile Ile
 1               5                  10                  15

Gln Val Leu Gln Ser Lys His Pro Gly Asp Phe Gly Ala Asp Ala Glu
             20                  25                  30

Gly Ala Met Asn Lys Ala Leu Glu Leu Phe Arg Lys Asp Met Ala Ser
         35                  40                  45

Asn Tyr Lys Glu Leu Gly Phe Gln Gly Gly Gly Ser Gly Gly Ala Pro
 50                  55                  60
```

(2) INFORMATION FOR SEQ ID NO: 25:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

```
Arg Trp Lys Val Arg Lys Ser Phe Phe Lys Leu Gln
 1               5                  10
```

(2) INFORMATION FOR SEQ ID NO: 26:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(ix) FEATURE:
    (A) NAME/KEY: CDS
    (B) LOCATION: 1..48
    (D) OTHER INFORMATION: /product= "endotoxin-neutralizing peptide"

(xi) SEQUENCE DESCRIPTION: SEQ ID NO: 26:

```
ATC ATG CGT TGG AAA GTT CGT AAA TCT TTC TTC AAA CTG CAG GAA TTC      48
Ile Met Arg Trp Lys Val Arg Lys Ser Phe Phe Lys Leu Gln Glu Phe
 1               5                  10                  15
```

(2) INFORMATION FOR SEQ ID NO: 27:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 27:

```
Ile Met Arg Trp Lys Val Arg Lys Ser Phe Phe Lys Leu Gln Glu Phe
 1               5                  10                  15
```

(2) INFORMATION FOR SEQ ID NO: 28:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(ix) FEATURE:
        (A) NAME/KEY: CDS
        (B) LOCATION: 1..42
        (D) OTHER INFORMATION: /product= "endotoxin-neutralizing peptide"

(xi) SEQUENCE DESCRIPTION: SEQ ID NO: 28:

```
GCG CCG CGT TGG AAA GTT CGT AAA TCT TTC TTC AAA CTG CAG              42
Ala Pro Arg Trp Lys Val Arg Lys Ser Phe Phe Lys Leu Gln
 1               5                  10

TGATAA                                                               48
```

(2) INFORMATION FOR SEQ ID NO: 29:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 29:

```
Ala Pro Arg Trp Lys Val Arg Lys Ser Phe Phe Lys Leu Gln
 1               5                  10
```

(2) INFORMATION FOR SEQ ID NO: 30:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(ix) FEATURE:
    (A) NAME/KEY: CDS
    (B) LOCATION: 1..24
    (D) OTHER INFORMATION: /product= "purification tail for
        IMAC"

(xi) SEQUENCE DESCRIPTION: SEQ ID NO: 30:

```
GCG CCG CAC CAC CAC CAC CAC CAC TGATAA                    30
Ala Pro His His His His His His
 1               5
```

(2) INFORMATION FOR SEQ ID NO: 31:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 31:

```
Ala Pro His His His His His His
 1               5
```

(2) INFORMATION FOR SEQ ID NO: 32:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: linear (ii) MOLECULE TYPE: protein (vi) ORIGINAL SOURCE:
        (A) ORGANISM: Macrobdella decora (xi) SEQUENCE DESCRIPTION: SEQ ID NO: 32:

```
Ala Pro Arg Leu Pro Gln Cys Gln Gly Asp Asp Gln Glu Lys Cys Leu
 1               5                  10                  15

Cys Asn Lys Asp Glu Cys Pro Pro Gly Gln Cys Arg Phe Pro Arg Gly
                20                  25                  30

Asp Ala Asp Pro Tyr Cys Glu
            35
```

(2) INFORMATION FOR SEQ ID NO: 33:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..126
        (D) OTHER INFORMATION: /product= "platelet aggregation
            inhibitor decorsin"

(xi) SEQUENCE DESCRIPTION: SEQ ID NO: 33:

```
GAT ATC GCT CCG CGT CTG CCG CAG TGC CAG GGT GAC GAC CAG GAA AAA        48
Asp Ile Ala Pro Arg Leu Pro Gln Cys Gln Gly Asp Asp Gln Glu Lys
 1               5                  10                  15

TGC CTG TGC AAC AAA GAC GAA TGC CCG CCG GGT CAG TGC CGT TTC CCG        96
Cys Leu Cys Asn Lys Asp Glu Cys Pro Pro Gly Gln Cys Arg Phe Pro
                20                  25                  30

CGT GGT GAC GCT GAC CCG TAC TGC GAA TTC                               126
Arg Gly Asp Ala Asp Pro Tyr Cys Glu Phe
            35                  40
```

(2) INFORMATION FOR SEQ ID NO: 34:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO: 34:

```
Asp Ile Ala Pro Arg Leu Pro Gln Cys Gln Gly Asp Asp Gln Glu Lys
 1               5                  10                  15

Cys Leu Cys Asn Lys Asp Glu Cys Pro Pro Gly Gln Cys Arg Phe Pro
                20                  25                  30

Arg Gly Asp Ala Asp Pro Tyr Cys Glu Phe
            35                  40
```

(2) INFORMATION FOR SEQ ID NO: 35:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic gene"

(ix) FEATURE:
        (A) NAME/KEY: CDS
        (B) LOCATION: 1..123
        (D) OTHER INFORMATION: /product= "platelet aggregation
            inhibitor decorsin"

(xi) SEQUENCE DESCRIPTION: SEQ ID NO: 35:

```
GCG CCG GCT CCG CGT CTG CCG CAG TGC CAG GGT GAC GAC CAG GAA AAA        48
Ala Pro Ala Pro Arg Leu Pro Gln Cys Gln Gly Asp Asp Gln Glu Lys
 1               5                  10                  15

TGC CTG TGC AAC AAA GAC GAA TGC CCG CCG GGT CAG TGC CGT TTC CCG        96
Cys Leu Cys Asn Lys Asp Glu Cys Pro Pro Gly Gln Cys Arg Phe Pro
                20                  25                  30

CGT GGC GAC GCT GAC CCG TAC TGC GAA TGATAA                            129
Arg Gly Asp Ala Asp Pro Tyr Cys Glu
            35                  40
```

(2) INFORMATION FOR SEQ ID NO: 36:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO: 36:

-continued

```
Ala Pro Ala Pro Arg Leu Pro Gln Cys Gln Gly Asp Asp Gln Glu Lys
 1           5                   10                  15
Cys Leu Cys Asn Lys Asp Glu Cys Pro Pro Gly Gln Cys Arg Phe Pro
            20                  25                  30
Arg Gly Asp Ala Asp Pro Tyr Cys Glu
            35              40
```

What is claimed is:

1. A fusion protein comprising, from amino-terminal to carboxy-terminal:
   a functional domain; and
   an assembly device, that is a segment of a hydrophobic core of a parent polypeptide, wherein said assembly device is capable of forming hetero-multimers with one or more different segments of said hydrophobic core of said parent polypeptide, and wherein said functional domain is not naturally associated with said assembly device.

2. The functional polypeptide of claim 1, wherein said assembly device is capable of forming a hetero-dimer with another segment of said parent polypeptide.

3. The functional polypeptide of claim 1, wherein said assembly device is capable of forming a hetero-trimer with two other segments of said parent polypeptide.

4. The functional polypeptide of claim 1, further comprising a second functional domain.

5. The functional polypeptide of claim 2, further comprising a second functional domain.

6. The functional polypeptide of claim 3, further comprising a second functional domain.

7. The functional polypeptide of claim 1, wherein said functional domain is an antibody fragment.

8. The functional polypeptide of claim 2, wherein said functional domain is an antibody fragment.

9. The functional polypeptide of claim 3, wherein said functional domain is an antibody fragment.

10. The functional polypeptide of claim 4, wherein said functional domain is an antibody fragment.

11. The functional polypeptide of claim 5, wherein said functional domain is an antibody fragment.

12. The functional polypeptide of claim 6, wherein said first functional domain is an antibody fragment.

13. The functional polypeptide of claim 2, wherein said parent polypeptide is ubiquitin, acyl-phosphatase, IL-2, or calbindin.

14. The functional polypeptide of claim 5, wherein said parent polypeptide is ubiquitin, acyl-phosphatase, IL-2, or calbindin.

15. The functional polypeptide of claim 3, wherein said parent polypeptide is apomyoglobin.

16. The functional polypeptide of claim 6, wherein said parent polypeptide is apomyoglobin.

17. A polypeptide complex comprising at least two fusion proteins according to claim 1.

18. A polypeptide complex comprising two fusion proteins according to claim 2.

19. A polypeptide complex comprising three fusion proteins according to claim 3.

20. A polypeptide complex comprising at least two fusion proteins according to claim 4.

21. A polypeptide complex comprising two fusion proteins according to claim 5.

22. A polypeptide complex comprising three fusion proteins according to claim 6.

23. A DNA sequence encoding the fusion protein of claim 1.

24. A vector comprising at least one DNA sequence of claim 23.

25. A host cell transformed with at least one vector of claim 24.

26. A method for the production of the fusion protein of claim 1, comprising the steps of: culturing the host cell according to claim 25 in a suitable medium, and recovering said fusion protein encoded by said host cell.

* * * * *